US006660252B2

(12) United States Patent
Matathia et al.

(10) Patent No.: US 6,660,252 B2
(45) Date of Patent: Dec. 9, 2003

(54) LOW EMULSIFIER MULTIPLE EMULSIONS

(75) Inventors: Michelle Matathia, Plainview, NY (US); Charles Craig Tadlock, Islip Terrace, NY (US)

(73) Assignee: Color Access, Inc., Melville, NY (US)

( * ) Notice: Subject to any disclaimer, the term of this patent is extended or adjusted under 35 U.S.C. 154(b) by 93 days.

(21) Appl. No.: 09/795,423

(22) Filed: Feb. 28, 2001

(65) Prior Publication Data

US 2002/0004532 A1 Jan. 10, 2002

Related U.S. Application Data

(63) Continuation-in-part of application No. 09/580,743, filed on May 26, 2000.

(51) Int. Cl.$^7$ .......................... A61K 7/021; A61K 7/06; A61K 9/113; B01F 17/34
(52) U.S. Cl. .................. 424/63; 424/70.12; 424/70.13; 514/941; 516/54; 516/74; 516/902; 526/932
(58) Field of Search .................... 516/54, 74, 902; 526/932, 941; 424/70.12, 63, 64, 70.13

(56) References Cited

U.S. PATENT DOCUMENTS

| 5,196,187 | A | * | 3/1993 | Nicoll et al. ............ 514/941 X |
| 5,217,648 | A | * | 6/1993 | Beissinger et al. ............ 516/54 |
| 5,322,704 | A | * | 6/1994 | Gaonkar .................... 516/54 X |
| 5,391,321 | A | * | 2/1995 | Grüning et al. ......... 514/941 X |
| 5,567,426 | A | * | 10/1996 | Nadaud et al. ...... 424/70.12 X |
| 5,750,124 | A | * | 5/1998 | Gohla et al. ............ 514/941 X |
| 5,942,216 | A | * | 8/1999 | Herb et al. ................ 516/54 X |
| 5,958,435 | A | * | 9/1999 | Fructus ...................... 516/54 X |
| 6,022,547 | A | * | 2/2000 | Herb et al. ............. 514/941 X |
| 6,150,425 | A | * | 11/2000 | Sekine et al. ........... 514/941 X |
| 6,171,600 | B1 | * | 1/2001 | Dahms ...................... 516/54 X |
| 6,346,256 | B1 | * | 2/2002 | Simon ................. 424/70.12 X |
| 6,358,500 | B1 | * | 3/2002 | Simon ...................... 424/70.12 |

FOREIGN PATENT DOCUMENTS

| EP | 0715842 | 6/1996 | ............ A61K/7/00 |
| EP | 0779071 | 6/1997 | ............ A61K/9/113 |
| EP | 0780112 | 6/1997 | ............ A61K/7/00 |
| EP | 0908170 | 4/1999 | ............ A61K/7/00 |
| EP | 0985402 | 1/2000 | ............ A61K/7/00 |
| EP | 09790741 | 1/2000 | ............ B01F/13/00 |
| WO | WO 01/85108 | 11/2001 | ............ A61K/7/06 |

* cited by examiner

Primary Examiner—Richard D. Lovering
(74) Attorney, Agent, or Firm—Karen A. Lowney, Esq.

(57) ABSTRACT

The invention relates to multiple emulsions comprising a primary emulsion in an external phase, and comprising a principle water phase and a principle oil phase, the multiple emulsion containing no more than about 1% of an emulsifier having an HLB of about 16 to about 20.

17 Claims, No Drawings

LOW EMULSIFIER MULTIPLE EMULSIONS

This application is a Continuation-In-Part of commonly assigned, pending application Ser. No. 09/580,743, filed May 26, 2000, which is incorporated by reference herein, in its entirety.

FIELD OF THE INVENTION

The present invention relates to cosmetic and pharmaceutical compositions. More specifically, the invention relates to cosmetic and pharmaceutical emulsions.

BACKGROUND OF THE INVENTION

One of the most common vehicles for cosmetic and pharmaceutical products is the emulsion. Because they are formed by the dispersion of an oil in water, or water in an oil, emulsions provide great versatility in the delivery of different types of active ingredients. A single oil and water formulation can be used to deliver both oil soluble and water soluble active components, thereby giving the formulation a range of potential activity that cannot be matched by a single phase system.

An obvious disadvantage to emulsions is that the materials to be combined are not inherently compatible. The natural tendency of oil and water to separate when mixed must therefore be compensated for by addition of further components to the formulation to aid in keeping the components of the dispersion together. Typically, maintenance of a stable dispersion requires the addition of substantial amounts of emulsion stabilizers and/or emulsifiers. The necessity of addition of these materials not only adds cost to the final product, but also has an effect on the quality of the final product, by affecting the way the emulsion breaks, as well as how it feels on the skin. Use of large quantities of emulsifiers is particularly undesirable, as many consumers perceive these materials as being potentially harsh or irritating to the skin.

The problem in further magnified when the formulation desired is a multiple emulsion, for example, a water-in-oil-in water, or oil-in-water-in-oil. Such emulsions, when feasible, provide a multipurpose product, at least in principle permitting the inclusion of an even greater number of different actives or other cosmetic components, with varied incompatibilities to heat, other components, or one of the desired solvents. It also is a useful vehicle for delayed release of actives on and into the skin, by virtue of the necessity of passing through the multiple phases. However, in practice, despite their clear value, such emulsions are not frequently employed, as the additional phase introduces further problems with stability, and therefore, they frequently require the use of very large quantities of emulsifiers and/or emulsion stabilizers. Further, once a particular system is established, the addition of other materials to the stable emulsion will tend to destabilize it. Therefore, the full potential of the multiple emulsion has not been fully realized. The present invention, however, provides an advance in the preparation of low-emulsifier multiple emulsions.

SUMMARY OF THE INVENTION

The present invention relates to a stable oil and water multiple emulsion, the emulsion comprising less than about 1% of traditional emulsifiers, i.e., emulsifiers having an HLB of about 16–20. The multiple emulsion is formed from the combination of a standard two phase emulsion (water-in-oil or oil-in-water) and a single phase (water or oil). Preferably, the principle oil phase is thickened by the addition of an oil miscible polymer having polar moieties. In a preferred embodiment, particularly in the water-in-oil-in water type of emulsion, the viscosity of the two components, i.e., the primary emulsion and the external phase, are adjusted so as to be substantially the same. In such an embodiment, the viscosity of the principle water phase is adjusted by addition of a small amount, preferably less than 2%, of a water-miscible thickener with no emulsifying properties. Multiple emulsions prepared in this way are remarkably stable, and because of the low level of emulsifiers, very gentle to the skin.

DETAILED DESCRIPTION OF THE INVENTION

The emulsions of the invention are prepared in much the same way as other multiple emulsions are prepared. Initially, a water-in-oil or an oil-in-water emulsion is prepared according to standard procedure. For a standard emulsion, the water soluble ingredients are combined together in an aqueous vehicle, the oil soluble ingredients are combined in the oil vehicle, and the two phases are combined with a standard homogenizer. In the present case, the water and oil components can be any of the standard components that are ordinarily used for this purpose. The aqueous phase may be any cosmetically acceptable water based material, such as deionized water, or a floral water. The oil phase may be any cosmetically or pharmaceutically acceptable oil, such an oil being defined for the present purpose as any pharmaceutically or cosmetically acceptable material which is substantially insoluble in water. As the oils can perform different functions in the composition, the specific choice is dependent on the purpose for which it is intended. The oils may be volatile or non-volatile, or a mixture of both. For example, suitable volatile oils include, but are not limited to, both cyclic and linear silicones, such as octamethylcyclotetrasiloxane and decamethylcyclopentasiloxane; or straight or branched chain hydrocarbons having from 8–20 carbon atoms, such as decane, dodecane, tridecane, tetradecane, and C8–20 isoparaffins.

Non-volatile oils include, but are not limited to, vegetable oils, such as coconut oil, jojoba oil, corn oil, sunflower oil, palm oil, soybean oil; carboxylic acid esters such as isostearyl neopentanoate, cetyl octanoate, cetyl ricinoleate, octyl palmitate, dioctyl malate, coco-dicaprylate/caprate, decyl isostearate, myristyl myristate; animal oils such as lanolin and lanolin derivatives, tallow, mink oil or cholesterol; glyceryl esters, such as glyceryl stearate, glyceryl dioleate, glyceryl distearate, glyceryl linoleate, glyceryl myristate; non-volatile silicones, such as dimethicone, dimethiconol, dimethicone copolyol, phenyl trimethicone, methicone, simethicone; and nonvolatile hydrocarbons, such as isoparaffins, squalane, or petrolatum.

Although any oil can be used, and mixtures of different types of oils is contemplated, it is particularly preferred that the principle component of the oil phase be a silicone oil, particularly dimethicone, cyclomethicone, or a combination of both. Most preferably, the silicone portion of the emulsion should be about 15–50% of the total water-in-silicone emulsion. Incorporated into the oil phase is an oil-miscible polymer having polar moieties. The polymer provides some level of thickening, and also, because of the presence of the polar groups, assists holding together the water and oil phases, thereby conferring a substantial level of stabilization. Any polymer fitting this description can be used. A particularly preferred polymer for this purpose, especially in a silicone oil base, is a dimethicone copolyol crosspolymer. Material of this type can be purchased from Shin-Etsu Silicones, under the product name KSG21. Another example of a useful oil-phase thickener, which may be more appropriate for a non-silicone oil phase, is lanolin; although not strictly speaking a polymer, it has many of the characteristics of a polymer, with its high molecular weight and thickening properties. It is also oil-miscible, and yet has the requisite polar groups in the presence of fatty alcohols and esters. Therefore, when used in the present context, the term "polymer" will be understood to encompass this type of complex molecule as well. The polymer in absolute terms will be used in an amount suitable to the desired viscosity. Generally speaking, the polymer will be present in an amount greater than zero but no greater than 5%, preferably no greater than about 3%, more preferably no greater than about 2%, most preferably no greater than about 1%, by weight of the total multiple emulsion To prepare a water-in-silicone (or oil)-in water emulsion, the simple emulsion is added to a water phase which will serve as the external phase of the multiple emulsion. The proportion of emulsion to the water phase can be up to 50:50, but preferably is in the range of about 10–40:90–60 emulsion:water, and most preferably is in the range of about 30–40:70–60. In order to enhance the stability, the external water phase is also thickened with any water-miscible thickener, provided it does not have emulsifying properties. Examples of useful thickeners for use in the external water phase are gums, such as xanthan gum, carbomer, cellulosics, chitosan, starches, and the like. A particularly preferred thickener for the external water phase is an ammonium poly(acryldimethyltauramide-co-vinylformamide), also referred to as AMPS/VIFA copolymer, available commercially from Clariant Corporation, Charlotte, N.C. under the name trade name Aristoflex AVC®. The amount of thickener is not crucial, and in this type of emulsion will be used in an amount sufficient to give the desired viscosity.

Also added to the water phase, again in relatively small quantities, is a traditional emulsifier having an HLB in the range of about 16–20. The majority of emulsifiers falling into this category are ethoxylates, most frequently nonionic ethoxylated fatty acids, esters, sorbitan esters, oils and alkylphenols. However, any type of liquid emulsifier meeting the HLB requirement can be used. Examples of other emulsifiers of this type can be found in McCutcheon's, Vol 1: Emulsifiers & Detergents, 2000, the contents of which are incorporated herein by reference. Particularly preferred for use in the present invention is Tween 20 (POE (20) sorbitan monolaurate) with an HLB of about 16.7. Unlike more typical multiple emulsions, there is very little of this standard emulsifier needed to hold the emulsion together. Overall, there will ordinarily be no more than 2% total emulsifier of any kind in the multiple emulsion, and preferably no more than 1%, more preferably 0.5% or less (by weight of the multiple emulsion) of a standard ethoxylated emulsifier. The high HLB emulsifier is added to the principle water phase after gelling and just prior to combination with the water-in-oil primary emulsion. The two entities are then combined by static mixing, and mixed to homogeneity.

The foregoing system has been described in terms of a water-in-oil-in-water emulsion. However, the system can also be used to prepare an oil-in-water-in-oil emulsion. In this scenario, a primary oil-in-water emulsion is prepared, preferably by high shear mixing to create a water-thin emulsion, such as described, for example, in Example 2B below, or in co-pending U.S. patent application Ser. No. 09/580,743, the contents of which are incorporated herein by reference. This primary emulsion is optionally thickened as described above for the water phase of the water-in-oil-in-water emulsion. The primary emulsion is then added to the principle oil phase thickened with an oil-miscible absorbent polymer, preferably a dimethicone copolyol crosspolymer, as described for the water-in-oil-in-water emulsion, and mixed by static mixing. The oil-in-water-in-oil is somewhat more stable than the water-in-oil-in-water; therefore, this multiple emulsion can be prepared with substantially no added traditional emulsifier. In addition, the primary emulsion can be added to the external phase in a broader range, generally about 10–60:90–40 emulsion:external oil phase. At the higher levels of the range, however, the amount of polymer in the external phase should be increased accordingly to the higher end of the appropriate range.

Similarly, it is possible to create a quadruple emulsion using the same general methodology. To prepare this type of multiple emulsion, a water-thin oil-in-water emulsion is prepared as described above, and thickened as if it were the water phase of the triple emulsion first described. A water-in-oil emulsion, thickened with the oil-miscible polymer, is added to the thickened oil-in-water emulsion, and mixed to homogeneity with static mixing.

The emulsions prepared as described above are highly stable. However, additional stability, particularly with the water-in-oil-in water emulsion, can be obtained by matching the viscosities of the primary emulsion and the external phase. As already noted above, the overall viscosity of the product is a matter of choice, depending on the intended final use of the product. However, it is preferred, within that framework, that the viscosities of the emulsion and external phase be matched to within about 10%, viscosity being measured in centipoise by a Brookfield viscometer.

The emulsions of the present invention provide a number of advantages over traditional multiple emulsions. For example, they are prepared with a minimum quantity of emulsifiers and thickeners, the presence of which can alter the mildness and the desired elegant feel of the final product. The system also permits for a greater concentration of the primary emulsion (10–50%) in the multiple emulsion, thereby permitting a broader variety of textures, and a broader appeal to a wide range of consumers. As with other multiple emulsions, these can be used to deliver a number of different types of active materials, partitioned among the various phases of the final product. This can be particularly important in a system in which there are several actives that may not be compatible together, or that may not exhibit optimum activity in the same environment. The multiple emulsions can also be used as a novel delivery system for pigment, in which the pigment is incorporated into the internal phase of the emulsion, and the color developed after rubbing on the skin. The emulsions can essentially be used for any type of application in which a standard emulsion is routinely used, for example, skin care products, pharmaceutical or veterinary drug delivery, sunscreens/self-tanners, rinse-off hair conditions, and liquid makeups.

The invention will be further illustrated by the following non-limiting examples.

EXAMPLES

Example 1

A. Preparation of Primary Emulsion for a Triple Emulsion Foundation

| Material | Weight % |
|---|---|
| Phase 1 | |
| Cyclomethicone/dimethicone | 5.00 |
| Phenyl trimethicone | 5.00 |
| Dimethicone/dimethicone copolyol Crosspolymer (75:25) | 7.00 |
| Cyclomethicone | 1.00 |
| Dimethicone | 8.00 |
| Pigment | 5.00 |
| Elefac I-205 | 3.00 |
| Phase 2 | |
| Xanthan gum | 0.20 |
| Butylene glycol | 5.00 |
| Distilled water | 59.80 |
| Sodium chloride | 1.00 |

Phase 1 materials are combined with sweep mixing in a primary vessel. The xanthan gum and butylene glycol are combined in an auxiliary vessel and mixed under propeller mixing until homogeneous. The remaining Phase 2 materials are added to the auxiliary vessel and heated to 40° C., mixing with propeller. Phase 2 materials are added to Phase 1 materials, and then homomixed to desired viscosity.

B. Preparation of Triple Emulsion

| | Material | Weight %* |
|---|---|---|
| (i) | external water phase | |
| | Distilled water | 49.70 |
| | Glycerine/glyceryl polyacrylate | 1.00 |
| | Sodium hyaluronate (2% solution) | 10.00 |
| | Dimethicone copolyol | 0.50 |
| | Glycereth-26 | 2.00 |
| | 1,3 butylene glycol | 5.00 |
| | Tween 20 | 0.30 |
| (ii) | thickener AMPS/VIFA copolymer** | 1.50 |
| (iii) | primary emulsion composition of Example 1A | 30.00 |

*of total multiple emulsion
**ammonium poly(acryldimethyltauramide-co-vinylformamide)-Aristoflex AVC ®, Clariant Corporation The materials of the external water phase are combined and heated to 45° C. with propeller mixing. With static mixing, the thickener is added to the water phase and mixed until a clear gel is formed. The primary emulsion is added to the previously combined materials under continuous static mixing until mixed to completion.

Example 2

Preparation of a quadruple emulsion of the invention

A. A water-in-oil primary emulsion is prepared as follows:

| Material | Weight % |
|---|---|
| Phase I | |
| Cyclomethicone/dimethicone | 5.00 |
| Phenyltrimethicone | 5.00 |
| Dimethicone/copolyol crosspolymer | 7.00 |
| Cyclomethicone | 1.00 |
| Dimethicone | 8.00 |
| Phase II | |
| Xanthan gum | 0.20 |
| Deionized water | 64.30 |
| Sodium chloride | 1.00 |
| Butylene glycol | 5.00 |
| Parabens | 0.50 |

The oil phase ingredients are combined together, and the water phase ingredients are combined together. The water phase is then slowly added to the oil phase, and homogenized until uniform.

B. Water-thin, low emulsifier emulsion serving as the external "water" phase is prepared as follows:

| Material | Weight % |
|---|---|
| Phase I | |
| deionized water | 32.50 |
| Arlatone Versaflex High Performance Emulsion Stabilizer* | 1.00 |
| Phase II | |
| Deionized water | 32.05 |
| Methyl paraben | 0.20 |
| Butylene glycol | 3.00 |
| Phenoxyethanol | 0.40 |
| Phase III | |
| Behenyl alcohol | 0.75 |
| Pentaerythrityl tetraethylhexanoate | 30.00 |
| Beta-carotene | 0.10 |

*Uniqema

In Phase I, the emulsifier is added to water at 80° C. Phase II ingredients are added to Phase I at 80° C. Phase III ingredients are combined and then homomixed with Phase I and II ingredients at greater than 10,000 rpm for 5 minutes. The combined components are then passed through a microfluidizer at 16,000 psi three times to achieve a water-thin emulsion.

C. Quadruple Emulsion

| Material | Weight % |
|---|---|
| Polysorbate 20 | 0.20 |
| Carbopol | 1.00 |
| O/W emulsion from B. | 78.80 |
| W/O emulsion from A. | 20.00 |

The O/W emulsion is combined with the Carbopol using static mixing. Polysorbate 20 is then added. The W/O emulsion is slowly added to the O/W phase utilizing static mixing. When the addition is complete, the mixing is continued for about 5 minutes until the multiple emulsion is uniform.

What we claim is:

1. A stable multiple emulsion comprising a primary emulsion in an external phase, and comprising a principal water phase and a principal oil phase, the multiple emulsion containing no more than about 1% of an emulsifier having an HLB of about 16 to about 20, wherein the principal water phase is thickened an AMPS/VIFA copolymer.

2. The emulsion of claim 1 in which the principal oil phase is thickened with an oil-miscible polymer having polar moieties.

3. The emulsion of claim 2 which is a water-in-oil-in water emulsion.

4. The emulsion of claim 2 in which the principle oil phase comprises primarily silicone oil.

5. The emulsion of claim 4 in which the polymer is a dimethicone copolyol crosspolymer.

6. A stable multiple emulsion comprising a primary emulsion in an external phase, and comprising a principal water phase and a principal oil phase, the multiple emulsion containing no more than about 1% of an emulsifier having an HLB of about 16 to about 20, in which the viscosity of the primary emulsion and the viscosity of the external phase are matched to within about 10%.

7. The emulsion of claim 6 in which the emulsion is a water-in-oil-in water emulsion.

8. A stable multiple emulsion comprising a primary emulsion in an external phase, and comprising a principle water phase and a principle oil phase, the principle water phase being thickened with a water miscible thickener, and the principle oil phase being thickened with an oil-miscible polymer having polar moieties, the viscosity of the primary emulsion and the viscosity of the external phase being matched to within about 10%, and the multiple emulsion containing no more than about 1% of an emulsifier having an HLB of about 16 to about 20.

9. The emulsion of claim 8 which is a quadruple emulsion.

10. The emulsion of claim 8 in which the principle oil phase comprises silicone and the thickener is dimethicone/dimethicone copolyol crosspolymer.

11. The emulsion of claim 8 in which the water miscible thickener is selected from the group consisting of gums, carbomer, cellulosics, chitosan, and starches.

12. The emulsion of claim 11 in which the thickener is AMPS/VIFA copolymer.

13. The emulsion of claim 8 which is a triple emulsion.

14. The emulsion of claim 13 which is an oil-in-water-in-oil emulsion.

15. The emulsion of claim 13 which is a water-in-oil-in-water emulsion.

16. A stable multiple emulsion capable of conferring color to skin comprising a primary emulsion in an external phase, and comprising a principal water phase and a principal oil phase, the multiple emulsion containing no more than about 1% of an emulsifier having an HLB of about 16 to about 20, which multiple emulsion comprises pigment, wherein the pigment is not incorporated into the external phase, and the color resulting from the pigment is developed only after rubbing on the skin.

17. A stable multiple emulsion comprising a primary emulsion in an external phase, and comprising a principal water phase and a principal oil phase, the multiple emulsion containing no more than about 1% of an emulsifier having an HLB of about 16 to about 20, wherein the emulsion is a quadruple emulsion.

* * * * *